United States Patent [19]

Suda et al.

[11] 4,044,052
[45] Aug. 23, 1977

[54] PROCESS FOR RECOVERY OF UREA FROM ITS PHENOLIC SOLUTION

[75] Inventors: Hideaki Suda, Takaishi; Iwao Dohgane, Nishinomiya; Hirokazu Hosaka, Minoo, all of Japan

[73] Assignee: Sumitomo Chemical Company, Limited, Japan

[21] Appl. No.: 578,661

[22] Filed: May 19, 1975

Related U.S. Application Data

[63] Continuation of Ser. No. 303,614, Nov. 3, 1972, abandoned.

[51] Int. Cl.² .................... C07C 102/00; C07B 21/00
[52] U.S. Cl. ........................ 260/96.5 C; 260/555 R; 260/96.5 R
[58] Field of Search .............. 260/96.5 C, 96.5 R, 260/555 B, 555 R

[56] References Cited

U.S. PATENT DOCUMENTS

| | | | |
|---|---|---|---|
| 1,830,859 | 10/1931 | Schotte et al. | 260/555 |
| 2,549,372 | 4/1951 | Fetterly | 260/96.5 R |
| 2,642,378 | 6/1953 | Barnes | 260/96.5 C |
| 3,462,498 | 8/1969 | Lowe et al. | 260/96.5 U |
| 3,855,195 | 12/1974 | Suda et al. | 260/96.5 C |

FOREIGN PATENT DOCUMENTS 770,234  7/1971  Belgium

OTHER PUBLICATIONS

Merck Index – 6th Ed. – (1952) – pp. 988, 739, 282, 283.
Weissberger, "Physical Methods", Part I, 3rd Ed., (1959) p. 347.
Condensed Chemical Dictionary – Hawley – 1974.

*Primary Examiner*—G. O. Peters
*Assistant Examiner*—Eugene T. Wheelock
*Attorney, Agent, or Firm*—Birch, Stewart, Kolasch and Birch

[57] ABSTRACT

A process for recovery of urea from a phenolic solution thereof which comprises adding an organic solvent selected from the group consisting of aliphatic amides, ethers, carbon disulfide and dimethylsulfoxide to the said phenolic solution and collecting the separated crystals of urea from the resultant mixture. The process is characteristic in recovering urea in the solid state without the use of water but a particular organic solvent.

7 Claims, No Drawings

PROCESS FOR RECOVERY OF UREA FROM ITS PHENOLIC SOLUTION

This application is a continuation of application Ser. No. 303,614, filed on Nov. 3, 1972 now abandoned.

The present invention relates to a process for the recovery of urea from a phenolic solution thereof. More particularly, it relates to a process for recovery of urea in the solid state from its phenolic solution using a particular organic solvent.

For recovery of urea from its solution in a phenolic solvent, there has heretofore been used water, because of its high solubility. In general, however, urea is relatively soluble in various phenolic solvents so that the extraction with water is not of a good efficiency. Further, various phenolic solvents show a considerable solubility in water so that the loss of the phenolic solvents is large, and the waste water containing urea and the phenolic solvents causes environmental pollution problems.

In order to overcome the defects as seen in the conventional recovery procedure using water, extensive studies have been made. As the result, it has been found that some particular organic solvents are quite effective in separating urea in the solid state, i.e. as crystals, from its solution in a phenolic solvent.

According to the present invention, a particular organic solvent selected from the group consisting of aliphatic amides, ethers, carbon disulfide and dimethylsulfoxide is added to a solution of urea in a phenolic solvent and the separated crystals of urea are collected from the resulting mixture.

The term "phenolic solvent" herein used is intended to mean a phenol and its mixture with any other organic solvent. Examples of the phenol are phenol, o-cresol, m-cresol, p-cresol, resorcinol, hydroquinone, xylenol, etc. Examples of the other organic solvent are benzene, toluene, xylene, etc.

The particular organic solvent to be used in the present invention is an aliphatic amide, an ether, carbon disulfide or dimethylsulfoxide. Examples of the aliphatic amide are N,N-dimethylformamide, N,N-dimethylacetamide, hexamethylphosphoric triamide, pyrrolidones, etc. Examples of the ether are dimethyl ether, diethyl ether, dipropyl ether, diisopropyl ether, dioxane, tetrahydrofuran, etc.

The amount of the particular organic solvent to be added is varied with the amounts of the phenolic solvent and of the urea dissolved therein and may be usually from 0.3 to 3.0 times in weight of that of the phenolic solution of urea to be treated.

The addition of the particular organic solvent is usually made at a temperature from −5° to 40° C. The separation of the crystals of urea is completed normally within a period of 10 minutes to 5 hours, in most cases within about 30 minutes, during which the mixture may be stirred.

The process of the invention is applicable to the recovery of urea from its solution in a phenolic solvent as well as the elimination of urea from a phenolic solvent contaminated therewith.

Therefore, the present invention also relates to an improvement on a process for the separation of m-cresol from its mixture with any other cresol. More specifically, m-cresol can be recovered from its mixture with any other cresol by treating the mixture with urea in the presence of an organic solvent at a lower temperature to form a molecular compound of m-cresol and urea, separating the molecular compound from the resulting mixture, decomposing the molecular compound at a higher temperature to m-cresol and urea and separating m-cresol from the resultant mixture (see Belgian Pat. No. 770,234, which corresponds to U.S. Pat. No. 3,855,195, the disclosure of which is expressly incorporated herein). In the final step of such process, the mixture of m-cresol and urea is usually treated with an appropriate organic solvent (e.g. toluene) so as to extract the m-cresol. The extract is then fractionally distilled to recover the organic solvent and m-cresol separately. In this fractional distillation, the urea contaminated in the extract is decomposed by heat, thereby making the recovered m-cresol impure. In order to avoid such trouble, the extract is often washed with water to eliminate the contaminating urea. As mentioned above, however, urea is considerably soluble in m-cresol, and it is necessary to use a large amount of water for attaining the satisfactory elimination of urea. Moreover, m-cresol is relatively soluble in water so that the loss of m-cresol is great. Thus, the washing with water is not of a good efficiency. In addition, the urea is recovered in the form of a very dilute aqueous solution and is therefore not amenable to repeated use.

In the application of the process of this invention, the particular organic solvent (e.g. diethyl ether) is added to the said extract instead of treating with water so that the urea dissolved therein is separated. The separated urea is collected from the resulting mixture by a conventional procedure such as centrifugation or pressure filtration. Thus, the recovery or elimination or urea can be attained in a nonaqueous system by a simple operation, and the collected urea is in the solid state and may be subjected to repeated use with ease.

Practical and presently preferred embodiments of the present invention are illustratively shown in the following Examples.

EXAMPLES 1 to 6

To 1,000 grams of a toluene solution containing 400 grams of cresols, where 25 grams or 50 grams of urea were dissolved, was added tetrahydrofuran (hereinafter referred to as "THF") while stirring. Upon the addition, the solution turned turbid, and the crystals of urea began to precipitate. After the crystallization was completed, the resulting mixture was filtered to collect the crystals. The above procedures were done at 5° C.

The results are shown in Table 1.

Table 1

| Example | Amount of urea dissolved (Grams) | Amount of THF added (Grams) | Amount of urea separated (Grams) | Recovery rate of urea (Percent) |
|---|---|---|---|---|
| 1 | 50 | 300 | 45.3 | 90.6 |
| 2 | 50 | 500 | 46.4 | 92.8 |
| 3 | 50 | 1,000 | 47.7 | 95.4 |
| 4 | 50 | 2,000 | 47.9 | 95.8 |
| 5 | 25 | 500 | 23.0 | 91.8 |
| 6 | 25 | 1,000 | 23.7 | 94.6 |

EXAMPLES 7 to 16

To 1,000 grams of a benzene solution containing 200 grams of phenol, where 30 grams of urea were dissolved, was added N,N-dimethylformamide (hereinafter referred to as "DMF") while stirring to 0° C. The urea crystallized out was collected by filtration.

The results are shown in Table 2.

Table 2

| Example | Period of time for stirring (Minutes) | Amount of DMF added (Grams) | Amount of urea separated (Grams) | Recovery rate of urea (Percent) |
| --- | --- | --- | --- | --- |
| 7 | 10 | 800 | 24.5 | 81.7 |
| 8 | 30 | 800 | 27.8 | 92.7 |
| 9 | 60 | 800 | 28.2 | 94.0 |
| 10 | 90 | 800 | 28.2 | 94.0 |
| 11 | 120 | 800 | 28.4 | 94.7 |
| 12 | 10 | 1,500 | 26.5 | 88.3 |
| 13 | 30 | 1,500 | 27.9 | 93.0 |
| 14 | 60 | 1,500 | 28.5 | 95.0 |
| 15 | 90 | 1,500 | 28.7 | 95.7 |
| 16 | 120 | 1,500 | 28.8 | 96.0 |

EXAMPLE 17

To 1,000 grams of cresols wherein 70 grams or urea were dissolved, 1700 grams of isopropyl ether were added, and the resulting mixture was stirred while cooling at 8° C for one hour. The precipitated crystals were collected by filtration to give 74 grams of a wet cake of urea. The isopropyl ether was removed from the filtrate by distillation to give cresols wherein the content of urea was less than 2000 ppm.

What is claimed is:

1. A process for the recovery of urea from a phenolic solution thereof which comprises adding an organic solvent selected from the group consisting of N,N-dimethylformamide, N,N-dimethylacetamide, hexamethylphosphoric triamide, pyrrolidone, dimethyl ether, diethyl ether, dipropyl ether, diisopropyl ether, dioxane, tetrahydrofuran, carbon disulfide and dimethyl sulfoxide to the said phenolic solution at a temperature wherein crystals of urea are formed, and separating and collecting the resulting crystals of urea from the obtained mixture.

2. The process according to claim 1, wherein the amount of the organic solvent is 0.3 to 3.0 times in weight of that of the phenolic solution of urea.

3. The process according to claim 1 wherein the addition of the orgainc solvent is made at a temperature of from −5° C. to 40° C.

4. A process for the recovery of urea from a solution thereof in a phenolic solvent selected from the group consisting of phenol, o-cresol, m-cresol, p-cresol, resorcinol, hydroquinone and xylenol and mixtures of said phenolic solvent with benzene, toluene or xylene which comprises adding an organic solvent selected from the group consisting of N,N-diethylformamide, N,N-dimethylacetamide, hexamethylphosphoric triamide, pyrrolidone, dimethyl ether, diethyl ether, dipropyl ether, diisopropyl ether, dioxane, tetrahydrofuran, carbon disulfide and dimethyl sulfoxide to the said phenolic solution at a temperature of from −5° C. to 40° C., and separating and collecting the resulting crystals of urea from the obtained mixture.

5. In a process for separating m-cresol from a mixture with any other cresol which comprises the steps of (1) treating the said mixture with urea in the presence of an organic solvent at a temperature at which a molecular compound of m-cresol and urea is formed, (2) decomposing the molecular compound at a temperature higher than that employed in step (1) to give m-cresol and urea, (3) treating the resulting mixture with an organic solvent to extract m-cresol, and (4) fractionally distilling the extract to recover m-cresol and the organic solvent, the improvement which comprises adding an organic solvent selected from the group consisting of N,N-dimethylformamide, N,N-dimethylacetamide, hexamethylphosphoric triamide, pyrrolidone, dimethyl ether, diethyl ether, dipropyl ether, diisopropyl ether, dioxane, tetrahydrofuran, carbon disulfide and dimethyl sulfoxide to the said extract at a temperature wherein crystals of urea are formed prior to the fractional distillation step, collecting the resulting crystals of urea from the obtained mixture, and recycling the collected urea to the step (1).

6. The process according to claim 5, wherein the organic solvent is added to the extract at a temperature of from −5° to 40° C.

7. The process according to claim 6, wherein the temperature employed in step (1) is from −20° to 80° C.

* * * * *